United States Patent [19]

Seiler et al.

[11] Patent Number: 4,604,476

[45] Date of Patent: Aug. 5, 1986
:::

[54] ODOR-STABILIZED MERCAPTOALKYL ALKOXYSILANES AND A METHOD FOR THEIR PREPARATION

[75] Inventors: Claus-Dietrich Seiler, Rheinfelden; Hans-Joachim Vahlensieck, Wehr, both of Fed. Rep. of Germany

[73] Assignee: Dynamit Nobel AG, Troisdorf, Fed. Rep. of Germany

[21] Appl. No.: 683,385

[22] Filed: Dec. 19, 1984

[30] Foreign Application Priority Data

Feb. 23, 1984 [DE] Fed. Rep. of Germany ....... 3406534

[51] Int. Cl.$^4$ .............................................. C07F 7/08
[52] U.S. Cl. .................................................... 556/401
[58] Field of Search ........................................ 556/401

[56] References Cited

U.S. PATENT DOCUMENTS 3,211,794 10/1965 Coffield ......................... 556/401 X Primary Examiner—Paul F. Shaver
Attorney, Agent, or Firm—Felfe & Lynch

[57] ABSTRACT

The present invention relates to mercaptoalkyl alkoxysilanes and the permanent removal of the odorants contained in these compounds. These odorants form during the preparation of the said mercaptosilanes from halogen alkylsilanes with thiourea and ammonia. The removal of the odorants is performed by the admixture of compounds which contain oxirane groups. A subsequent purification, e.g., by distillation, after the addition of these compounds in accordance with the invention, is not necessary. The additive used in accordance with the invention also brings about a sustaining of the freedom from odor for several months.

8 Claims, No Drawings

ODOR-STABILIZED MERCAPTOALKYL ALKOXYSILANES AND A METHOD FOR THEIR PREPARATION

BACKGROUND OF THE INVENTION

The present invention concerns mercaptoalkyl alkoxysilanes which are free of malodorous byproducts, as well as a method for the permanent removal of these malodorous byproducts.

Mercaptoalkyl alkoxysilanes have many applications in the chemical industry. They are suitable for use, for example, as adhesivizers for the solution of special problems of adhesion between inorganic and organic substances or for the modification of silicones to broaden their applications. Disadvantageous in all applications is the strong, unpleasant odor which this product has on the basis of contaminating byproducts resulting from the technical production of these compounds. The mercaptoalkyl alkoxy-silanes are prepared, as a rule, by the reaction of halogen alkyl alkoxysilanes with thiourea and ammonia by the method described in German Federal Pat. No. 20 35 619. The unpleasant-smelling byproducts resulting from this method of preparation are contained in the end product in such small amounts that removing them by the obvious method of fractional or repeated distillation does not achieve the desired success, and the distillates obtained even by repeated fractional distillation are still extremely odorous and are not salable in this form.

The problem therefore existed of treating mercaptoalkyl alkoxysilanes such that they no longer have an unpleasant smell and the freedom from unpleasant odors lasts for a long time—several months if possible.

THE INVENTION

To solve this problem a method has been found for the removal of malodorous byproducts from mercaptoalkyl alkoxysilanes, which is characterized by mixing compounds containing oxirane groups into the previously manufactured mercaptoalkyl alkoxysilane.

The mercaptoalkyl alkoxysilane purified in this manner preserves its freedom from unpleasant odors for a long period of time on the basis of the presence of the oxirane-group-containing compounds. The subject matter of the present application, therefore, is also mercaptoalkyl alkoxysilanes which are stabilized as regards their odor by a content of compounds containing oxirane groups. The prevention of a recurrence of unpleasant odors is referred to hereinafter also as odor-stabilization.

The odor-causing compounds in the mercaptoalkyl alkoxysilanes which are eliminated by the additive in accordance with the invention are present in the mercaptosilanes in such small amounts that they are not detectable by known analytical methods. Their presence or absence can be detected only by the sense of smell. If unstabilized compounds are let stand for long periods of time the intensity of the odor often increases.

It is not necessary, after the admixture of the additives of the invention, to perform a separation of any reaction products that form or to re-distill the mercaptoalkyl alkoxysilane. After the admixture of the claimed compounds, the achieved odorlessness is sustained for several months without the performance of additional measures.

The odor-stabilization achieved by the addition of the claimed compounds is surprising in that it is known that mercaptans have a great reactivity against oxiranes, reacting with them to produce 2-hydroxyalkyl alkylsulfides. Use is made of this reactivity in analytical chemistry. This known reaction is unimportant in the present case in comparison to the reaction with the odorants. It is apparent that the presence of even minute amounts of oxiranes suffices to destroy any odorants that might form afterward, so that the addition of the claimed compounds also produces an odor-stabilizing effect.

Odor-stabilizers in the meaning of the present invention are all oxiranes which, aside from the oxirane group, have no reactive groupings in the molecule which are capable of entering preferentially into reactions with other reactive groups of the mercaptoalkyl silanes. Suitable compounds in the meaning of the invention are epoxyethane, epoxypropane, 1,2-epoxybutane, epoxycyclohexane, 1,2-epoxy-3-chloropropane, 2,3-epoxybutane, phenylepoxyethane, epoxycyclopentane, 1,2-epoxy-4-vinylcyclohexane, 3,4-epoxybutene(1), 1,2,3,4-diepoxybutane, allylglycide ether, glycidyloxypropyltrimethoxysilane, and others. The mercaptoalkyl alkoxysilanes to be stabilized include both mercaptoalkyl trialkoxysilanes and mercaptoalkyl (alkyl)dialkoxysilanes which can be prepared by the method of German Federal Pat. No. 20 35 619. The preferred compounds are the mercaptopropyl and mercaptoethyl alkoxysilanes. The preferred alkoxy groups are the methoxy and ethoxy groups. These compounds are liquid at room temperature. For their odor-stabilization in accordance with the invention, it is therefore recommendable to use liquid compounds containing oxirane groups. The preferred oxirane compound is 1,2-epoxybutane.

The amounts of the individual oxiranes to be used in each case are to be determined in different ways and from case to case. In general, amounts of 100 to 250 ppm with respect to the mercaptoalkyl alkoxysilane to be stabilized will suffice. It will do no harm to add amounts of up to 500 ppm or more, but, for reasons of economy, this will not usually be done. Mixtures of different oxiranes can also be added to the mercaptosilane for stabilization, provided that no reactions take place among them when they are mixed which might impair their effectiveness against the odorants.

The addition of the oxiranes can be performed at room temperature. Heating to counteract the offensive odor is possible, but not obligatory. Temperatures above 70°C. are to be avoided, since it is at this temperature that the above-mentioned competing reaction with the mercapto group of the silane can occur, which can lead to a reduction of the effectiveness of the oxirane. When such temperatures cannot be avoided, it is recommendable to use larger amounts of oxirane-group-containing compounds to eliminate the odorants.

COMPARATIVE EXAMPLE A

An enameled three-cubic-meter jacketed reaction vat which is equipped with a stirrer, a reflux condenser, a temperature measuring point and a gas introduction tube is filled with 1000 kg of 3-chloropropyltrimethoxysilane and 383 kg of thiourea. The mixture is heated, with stirring, to about 110° C. and brought to the reaction at this temperature by the introduction of ammonia. After the end of the reaction, the guanidine hydrochloride that has been formed as a byproduct of the reaction is separated from the reaction solution and the liquid content is vacuum-distilled.

A sample of the main run fraction (3-mercaptopropyltrimethoxysilane) is taken and tested for odor. A foul, evil-smelling odor is perceived.

A hydrolyzate of the main run fraction is prepared by hydrolyzing 8 g of the silane in 400 ml of water. After the hydrolysis a foul odor is smelled over the surface of the liquid, which is less intense than that emanating from the unhydrolyzed silane.

The main run fraction obtained is tested by gas chromatography. In the fractogram only peaks of compounds are found which are known not to be causes of odors.

COMPARATIVE EXAMPLE B

The main run fraction obtained in Comparative Example A is again subjected to a vacuum distillation. Immediately thereafter the tests described in Example A are repeated with the distillate. The results are the same as those of Comparative Example A, while only a slight reduction of the intensity of the odor is noted.

EXAMPLE 1

The main run fraction obtained in accordance with Comparative Example A is divided into several portions and to each portion there is added such an amount of 1,2-epoxybutane that mixtures result which have oxirane contents of 100, 250, 500 and 1000 ppm.

The tests performed in Comparative Example A are performed with the individual samples. Even in the sample containing only 100 ppm of oxirane virtually no unpleasant odor can be detected. The same applies to the hydrolyzate of this sample.

EXAMPLE 2

To portions of the main run fraction obtained in Comparative Example A such amounts of epichlorhydrin (1,2-epoxy-3-chloropropane) are added that mixtures are formed which have oxirane contents of 250, 500 and 1000 ppm.

The tests described in Comparative Example A are performed with the individual samples. Neither in the resultant samples nor in their hydrolyzates are any bad odors detectable.

EXAMPLE 3

To portions of the main run fraction produced in Comparative Example A such amounts of 3,4-epoxybutene(1) are added that mixtures are formed having oxirane contents of 250, 500 and 1000 ppm.

The tests described in Comparative Example A are performed with the individual portions. Neither in the resultant samples nor in the hydrolyzates prepared therefrom can any bad odor be detected.

COMPARATIVE EXAMPLE C

In an apparatus similar to Example A, and in the manner described therein, 114 parts of 2-chloroethyltriethoxysilane and 38.3 parts of thiourea, by weight, are reacted with ammonia. The further processing was performed in the manner described in Example 1.

A sample was taken from the main run fraction obtained (2-mercaptoethyltriethoxysilane) and examined for odor. A foul, evil-smelling odor emanates from it.

The main run fraction obtained is tested by gas chromatography. In the fractogram only peaks of compounds are found, of which it is known that they are not involved in causing odors.

COMPARATIVE EXAMPLE D

The main run fraction obtained in Comparative Example C is again subjected to a vacuum distillation. Immediately thereafter the examination for odor performed in Example C was performed on the distillate. The result is the same as in Example C, although a certain reduction in the intensity of the odor is noted.

EXAMPLES 4 to 6

Samples of the main run fraction from Comparative Example C are treated as in Examples 1 to 3 with the amounts of oxiranes given in these examples.

The odor testing was performed on the individual samples as described in Comparative Example C.

In no case could any offensive odor be detected.

EXAMPLE 7

The mercaptoalkylsilane/oxirane mixtures studied in Comparative Examples B and D were again subjected to tests for odors after standing for 6 and 12 months.

It was found that, in the samples from the two comparative examples a certain intensification of the odor had occurred, while the samples originating from Examples 1 to 6 remained unaltered as to odor.

It will be understood that the specification and examples are illustrative but not limitative of the present invention and that other embodiments within the spirit and scope of the invention will suggest themselves to those skilled in the art.

What is claimed is:

1. An odor-stabilized mercaptoalkyl alkoxysilane, comprising 100 to 500 ppm of compounds containing oxirane groups.

2. The odor-stabilized mercaptoalkyl alkoxysilane of claim 1, wherein the compound having an oxirane group is 1,2-epoxybutane, 1,2 epoxy-3-chloropropane, or 3,4 epoxybutane (1).

3. The odor-stabilized mercaptoalkyl alkoxysilanes of claim 2 wherein the compound having an oxirane group is 1,2-epoxybutane.

4. A method for the removal of malodorous by-products from mercaptosilanes, comprising the steps of mixing oxirane-group-containing compounds with the mercaptoalkyl alkoxysilanes.

5. The method of claim 4, wherein the compound containing oxirane groups is mixed with the mercaptoalkyl alkoxysilane at temperatures under 70° C. and in amounts of 100 to 500 ppm.

6. The method of claim 5 wherein 100 to 250 ppm of the compound containing oxirane groups are used.

7. The method of claim 5 wherein the compound containing oxirane groups is 1,2-epoxybutane, 1,2-epoxy-3-chloropropane, or 3,4 epoxybutane (1).

8. The method of claim 7 wherein the compound containing oxirane groups is 1,2-epoxybutane.

* * * * *